United States Patent [19]

Shiobara et al.

[11] Patent Number: 5,243,058
[45] Date of Patent: Sep. 7, 1993

[54] ALLYL OR PROPENYL GROUP-CONTAINING NAPHTHALENE DERIVATIVES

[75] Inventors: Toshio Shiobara, Annaka; Kazutoshi Tomiyoshi, Takasaki; Hisashi Shimizu; Manabu Narumi, both of Annaka, all of Japan

[73] Assignee: Shin-Etsu Chemical Co., Ltd., Tokyo, Japan

[21] Appl. No.: 824,967

[22] Filed: Jan. 24, 1992

[30] Foreign Application Priority Data

Jan. 25, 1991 [JP] Japan ................................. 3-025756

[51] Int. Cl.$^5$ .................... C07D 303/14; C07C 39/14; C07C 39/21
[52] U.S. Cl. ..................................... 549/555; 568/736; 568/737
[58] Field of Search ................ 549/555; 568/735, 736, 568/737

[56] References Cited

U.S. PATENT DOCUMENTS 3,555,117  1/1971  Stahly et al. .......................... 525/11

FOREIGN PATENT DOCUMENTS 0013258  12/1979  European Pat. Off.
0226648  12/1985  European Pat. Off.
440484A2  1/1991  European Pat. Off.
2012780  1/1979  United Kingdom.

OTHER PUBLICATIONS

Chemical Abstracts, vol. 95, No. 3, Jul. 29, 1981, pp. 24672, 24673, and 33050CS.
Chemical Abstracts, vol. 116, No. 12, Mar. 23, 1992, pp. 107561–107562.

Primary Examiner—Joseph L. Schofer
Assistant Examiner—Wu C. Cheng
Attorney, Agent, or Firm—Millen, White, Zelano, & Branigan

[57] ABSTRACT

A naphthalene derivative of the following general formula (1) having at least one allyl or propenyl group is described.

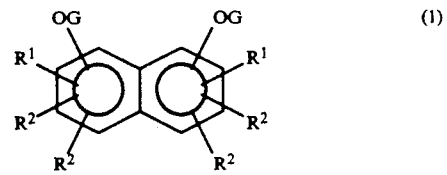

(1)

In the formula, each G represents a hydrogen atoms or

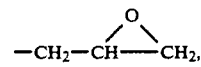

$R^1$'s independently represent a hydrogen atom, an allyl group or a propenyl group provided that at least one or $R^1$'s is an allyl group or a propenyl group, and $R^2$'s independently represent a hydrogen atom, an unsubstituted or substituted monovalent hydrocarbon group having from 1 to 6 carbon atoms, or a halogen atom. The derivative is useful for modifying curable resins or resin compositions to provide cured products which have a low water absorption, high strength and a high glass transition temperature. The derivative has good working properties and a good heat resistance.

1 Claim, 3 Drawing Sheets

ALLYL OR PROPENYL GROUP-CONTAINING NAPHTHALENE DERIVATIVES

BACKGROUND OF THE INVENTION

1. Field of the Invention

This invention relates to naphthalene derivatives which have an allyl or propenyl group or groups and which are effective when used in various curable resin compositions or as a modifier for various types of curable resins. The derivatives are excellent in working properties and heat resistance and are able to provide a cured product having high strength and high glass transition temperature.

2. Description of the Prior Art

Thermosetting resins have been widely used in the electric and structural fields as casting, dipping, laminating and molding materials. In recent years, there is a tendency toward severe conditions of use of the materials in these fields. Especially, importance is placed on the heat resistance and the low water absorptivity of the materials.

Known epoxy polymers which are typical of heat-resistant thermosetting resins include, for example, epoxidized phenol-novolac products (e.g. Epikote commercially available from Yuka-Shell Epoxy Co., Ltd.), epoxidize cresol-novolac products (e.g. EOCN available from Nippon Kayaku Co., Ltd.), methylenedianiline tetraepoxide, epoxidized tri- or tetra(hydroxyphenyl)alkanes and the like. There are also known as phenolic resins phenol-novolac resins, ortho-cresol-novolac resins, bis-phenol A, triphenol methane and the like resins.

Although the cured products obtained from these resins all exhibit relatively high heat resistance, the heat resistance is not always satisfactory, coupled with the disadvantage that in order to develop practical strength, heating at high temperatures over a long term is essentially required. In addition, the working properties are not satisfactory.

SUMMARY OF THE INVENTION

It is accordingly an object of the present invention to provide naphthalene derivatives which are effectively used as an ingredient for various resin compositions or as a modifier for various type of curable resins and which have good working properties and heat resistance.

It is another object of the present invention to provide thermally curable naphthalene derivatives which can yield cured products with a low water absorptivity and high strength when used in combination with resins having specific types of functional groups.

The above object can be achieved, according to the invention, by a naphthalene derivative of the following general formula (1) having at least one allyl or propenyl group

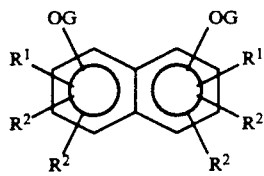 (1)

wherein each G represents a hydrogen atoms or

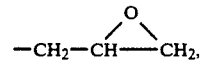

$R^1$'s independently represent a hydrogen atom, an allyl group or a propenyl group provided that at least one or $R^1$'s is an allyl group or a propenyl group, and $R^2$'s independently represent a hydrogen atom, an unsubstituted or substituted monovalent hydrocarbon group having from 1 to 6 carbon atoms, or a halogen atom.

The present invention is based on the finding that when, for example, dihydroxy-naphthalene is allylated or isomerized after the allylation and, optionally, epoxidized, novel naphthalene derivatives having at least one allyl or propenyl group shown in formula (1) are obtained. The derivatives have good working properties and moldability and can provide cured products which have good heat resistance and are not thermally deteriorated over a long term with a low water absorptivity and high strength. Therefore, the naphthalene derivatives can effectively be used as a thermosetting resin component for a semiconductor encapsulator. Further, the naphthalene derivatives having at least one allyl or propenyl group are highly reactive with organosilicon compounds having a $\equiv$SiH group and various types of organic compounds having a vinyl group, an epoxy group or a phenolic hydroxyl group. For instance, the naphthalene derivatives are very effective for modifying organosiloxanes, maleimide resins, epoxy resins and phenolic resins having such functional groups as mentioned above.

DETAILED DESCRIPTION AND EMBODIMENTS OF THE INVENTION

Figure 1:
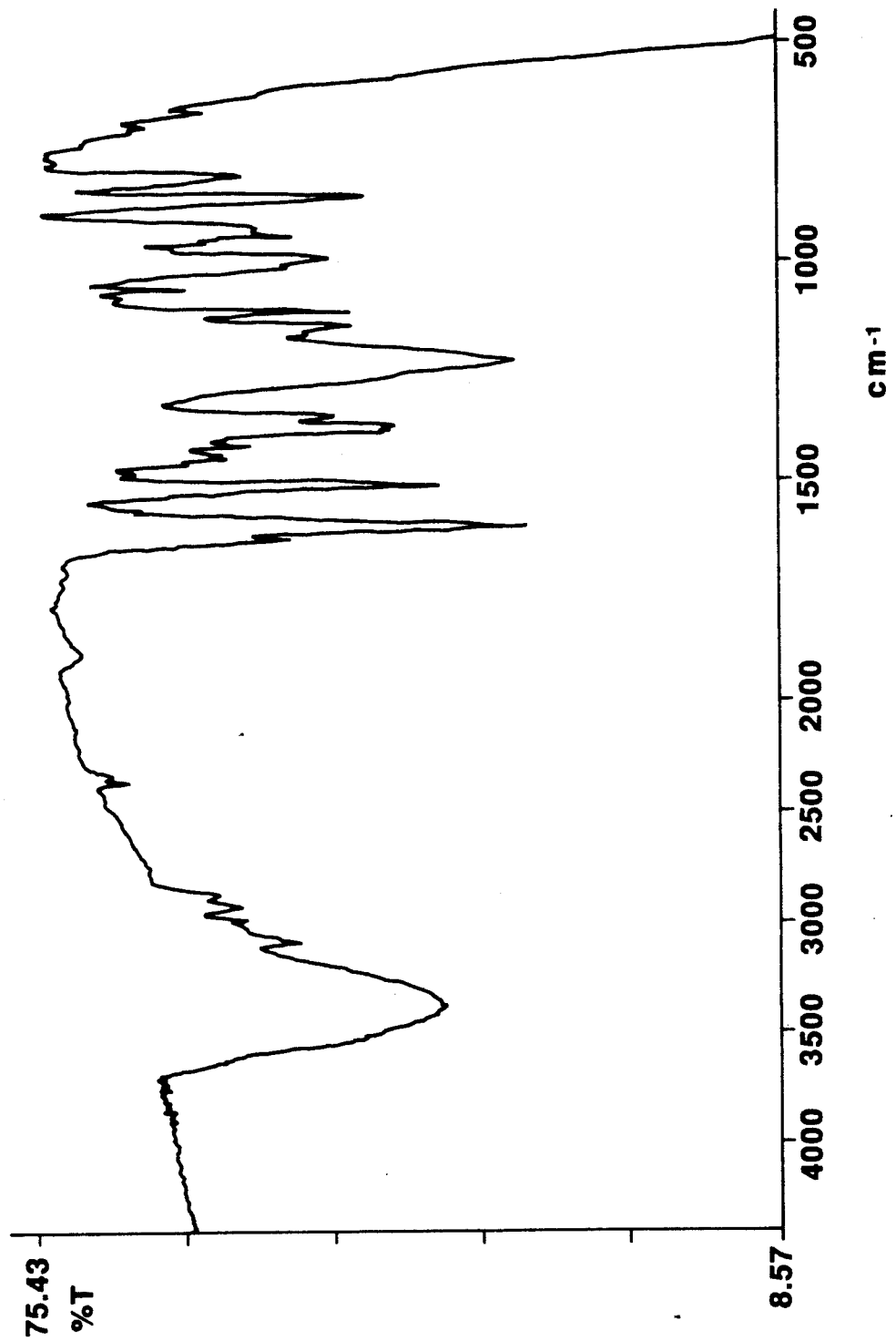
FIG. 1 is an IR absorption spectral chart of an allyl group-containing naphthalene derivative (compound B obtained in example) according to the present invention.

The novel naphthalene derivatives of the present invention are of the following general formula (1)

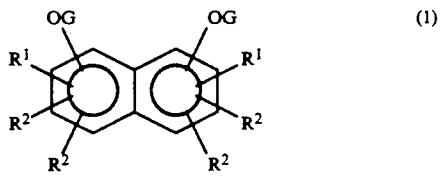 (1)

wherein each G represents a hydrogen atom or a glycidyl group, $R^1$'s independently represent a hydrogen atom, an allyl group or a propenyl group provided that at least one of $R^1$'S is an allyl group or a propenyl group, and $R^2$ is a hydrogen atom, an unsubstituted or substituted monovalent hydrocarbon group having from 1 to 6 carbon atoms, such as a methyl group, an ethyl group, a propyl group, a t-butyl group, an allyl group, a propenyl group or a phenyl group, or a halogen atom.

Since the naphthalene derivative of the formula (1) having an allyl or propenyl group has at least one allyl or propenyl group as a functional group in the molecule, radical reaction with vinyl compounds and addition reaction with organosiloxanes having a ≡SiH group and compounds having an epoxy group or a phenolic hydroxyl group are possible. Therefore, the derivatives are effective as a modifier for other epoxy resins, phenolic resins, maleimide resins and the like.

The allyl or propenyl group-containing naphthalene derivatives of the present invention can be readily prepared, for example, by allylating or allylating and then isomerizing dihydroxynaphthalene or obtain derivatives having a phenolic hydroxyl group. The phenolic hydroxyl group-bearing compounds may be further epoxidized to obtain derivatives having an epoxy group.

Starting dihydroxynaphthalenes may be properly used depending on the type of intended allyl or propenyl group-containing naphthalene derivatives, including, for example, 2,6-dihydroxynaphthalene.

Allylated dihydroxynaphthalene can be obtained by subjecting dihydroxynaphthalene to allyl etherification by any known technique, followed by Claisen rearrangement.

The isomerization of the allyl groups should preferably be effected by an alkaline isomerization technique described in Journal of American Chemical Society, pp. 1709-1713 (1956). By this, intended phenolic derivatives are obtained.

For epoxidization, there may be used known techniques using epichlorohydrin, NaOH and the like, thereby obtaining intended epoxidized derivatives.

More particularly, the phenolic and epoxidized derivatives of the following formulas (2) to (4) can be prepared, for example, according to the following reaction sequence.

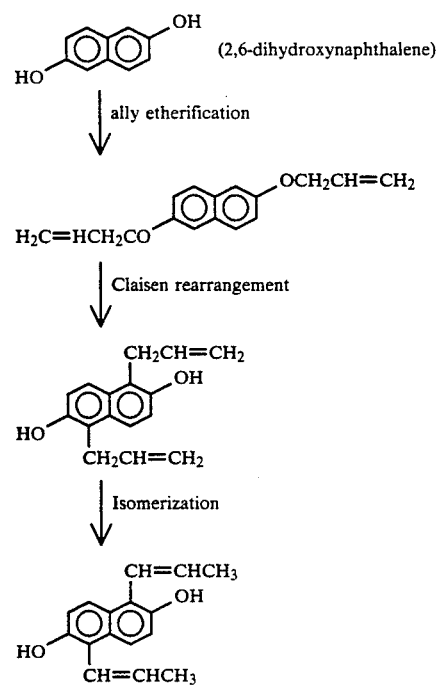

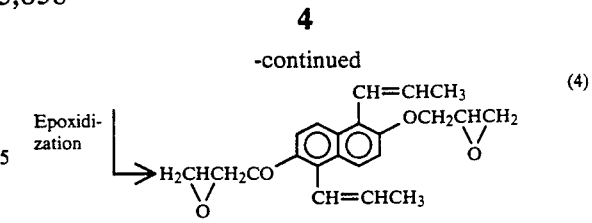

In the above reaction sequence, starting 2,6-dihydroxynaphthalene is allyl etherified, after which the allylated product obtained by the Claisen rearrangement is isomerized with an alkali to obtain a phenolic derivative, followed by epoxidization to obtain an epoxidized derivative.

The present invention is described in more detail by way of example, which should not be construed as limiting the invention.

EXAMPLE

Preparation of Compound A 192 g of 2,6-dihydroxynaphthalene was dissolved in acetone and placed along with 350 g of allyl bromide in a two liter four-necked flask equipped with a condenser, a thermometer and an agitator. While agitating, 208 g of potassium carbonate was introduced and dissolved, followed by reaction for 8 hours under agitation. After 8 hours, the solvent was removed by filtration and the resultant cake was dissolved in 0.8 liters of methyl isobutyl ketone, followed by washing and removal of the solvent by distillation to obtain 268 g of compound A having the following structural formula at a yield of 93.1%. The compound A was identified by NMR and IR analyses.

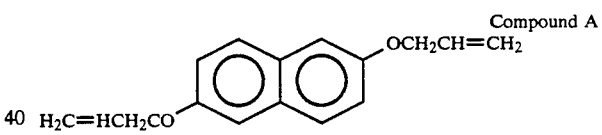

Preparation of Compound B 260 g of Compound A was heated in a one liter four-necked flask equipped with a condenser, a thermometer and an agitator in an atmosphere of nitrogen and reacted for 30 minutes to obtain 251.4 g of compound B having the following structural formula with a OH equivalent of 123 (theoretical: 120) at a yield of 96.7%. The compound B was identified by NMR and IR analyses. The IR absorption spectrum chart of compound B is shown in FIG. 1. The attributions of NMR spectra are shown below.

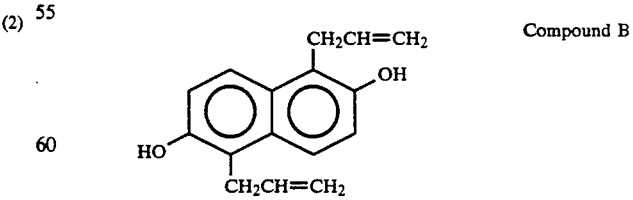

NMR spectra (solvent: $(CD_3)_2CO$, ppm ($\delta$)):

3.2-4.0: $[C_{10}H_4]-C\underline{H}_2-CH=CH_2$ 4.7-5.2: $-CH_2-CH=C\underline{H}_2$ -continued 5.5-6.2: $-CH_2-CH=CH_2$
6.7-8.3: $[C_{10}\underline{H}_4]$

Figure 2:
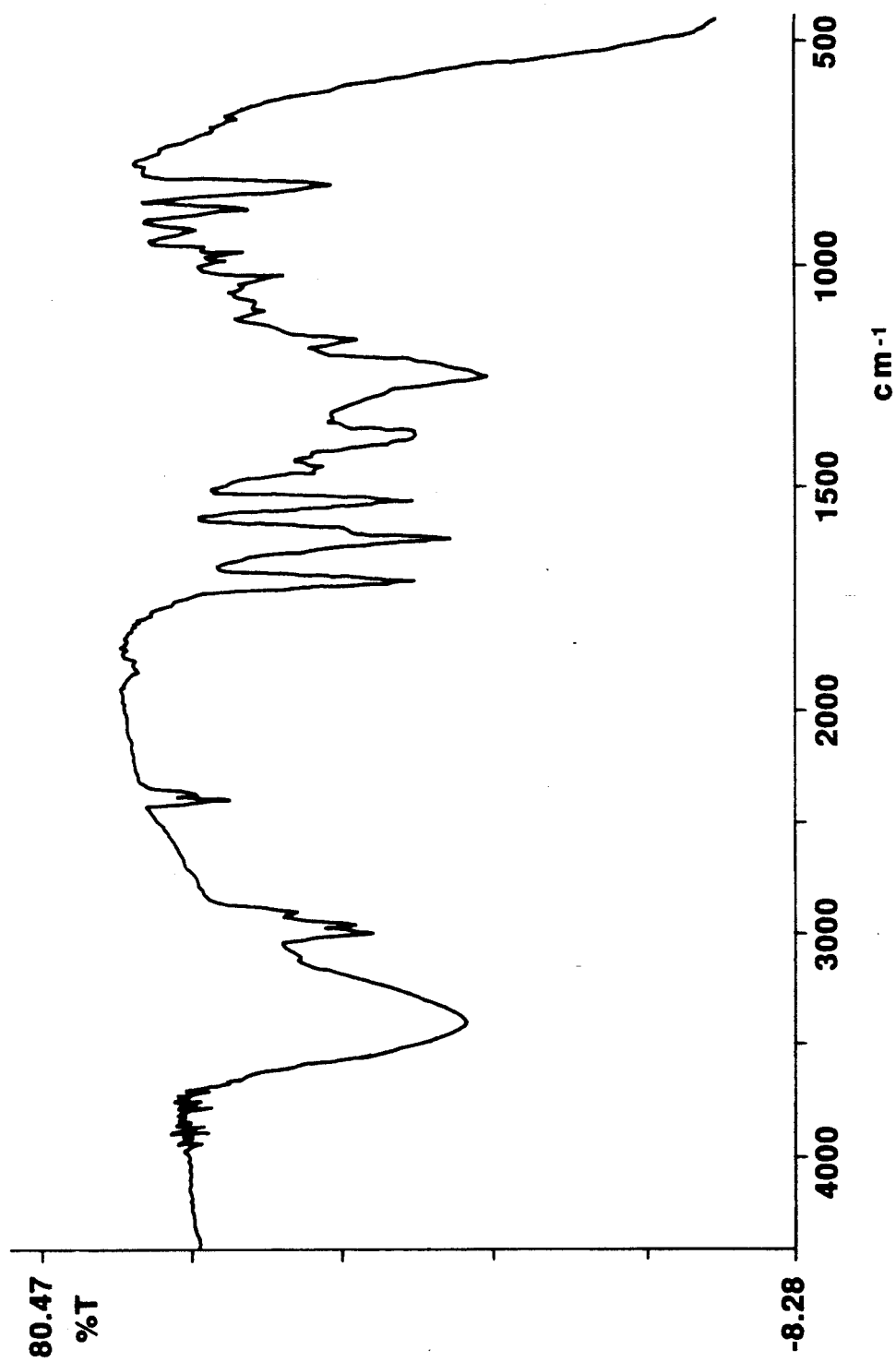
FIG. 2 is an IR absorption spectral chart of a propenyl group-containing naphthalene derivative (compound C obtained in example) according to the present invention.

Preparation of Compound C 240 g of Compound B, 770 g of methanol and 220 g of n-butanol were placed in a two-liter four-necked flask equipped with a condenser, a thermometer and an agitator and dissolved under agitation, to which 160 g of KOH was added and dissolved under heating conditions, followed by removal of methanol and reaction at 110° to 120° C. for 6 hours. After 6 hours, one liter of methyl isobutyl ketone was placed, followed by neutralization with hydrochloric acid and removal of the solvent by distillation to obtain 224.4 g of compound C with a OH equivalent of 127 (theoretical: 120) at a yield of 93.5%. The compound C was identified by NMR and IR analyses. The IR absorption spectrum chart of compound C is shown in FIG. 2. The attributions of NMR spectra are shown below.

Compound C

NMR spectra (solvent: $(CD_3)_2CO$, ppm ($\delta$)):
3.4: $-CH=CH-C\underline{H}_3$
6.7-8.3: $-[C_{10}\underline{H}_4]$, $-C\underline{H}=C\underline{H}-CH_3$

Figure 3:
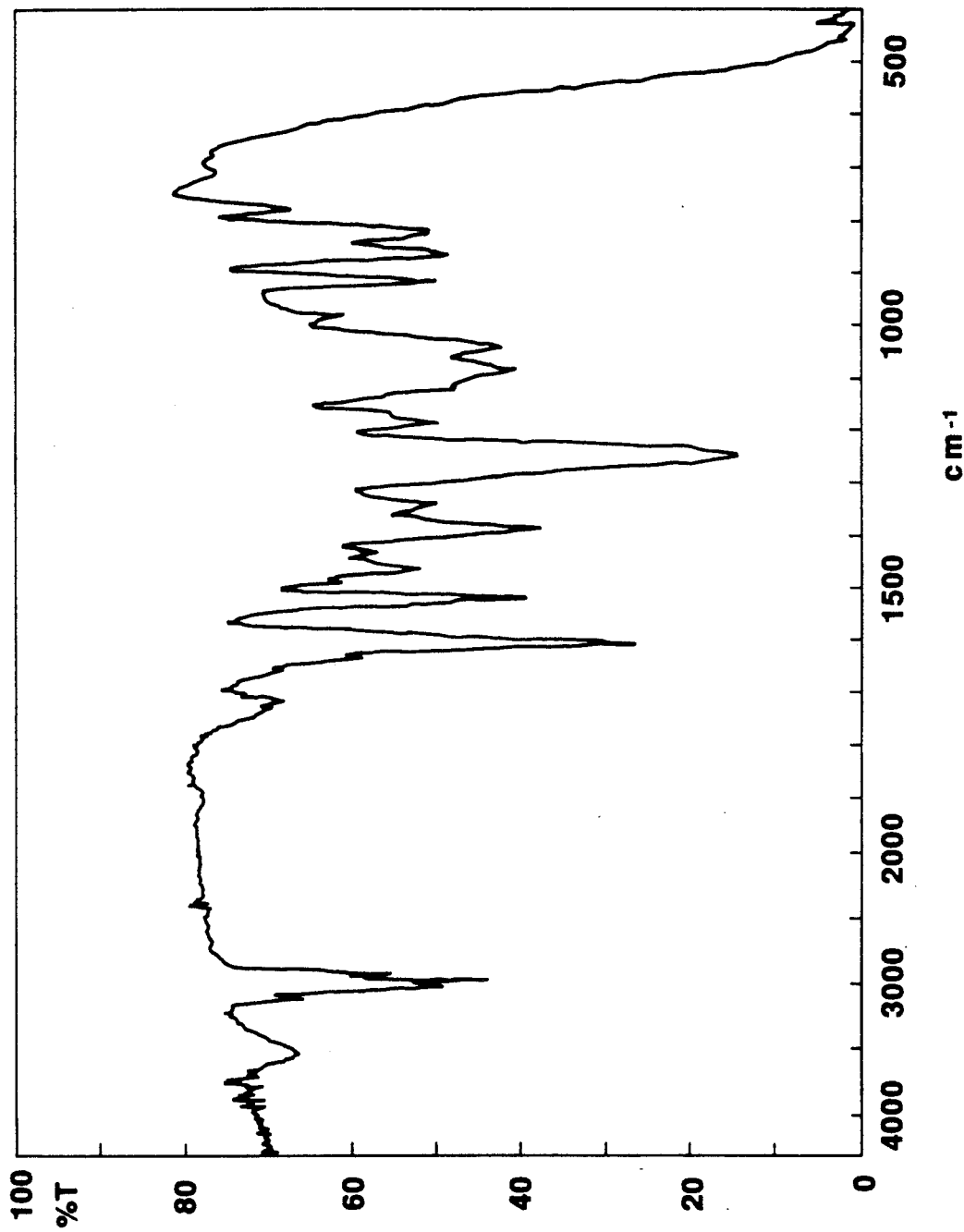
FIG. 3 is an IR absorption spectral chart of an epoxidized propenyl group-containing naphthalene derivative (compound D obtained in example) according to the present invention.

Preparation of Compound D 190 g of compound C, 780 g of epichlorohydrin and 0.72 g of cetyltrimethylammonium were placed in a two liter four-necked flask equipped with a condenser, a thermometer and an agitator, followed by agitation under reflux for 3 hours. Thereafter, 120 g of NaOH (50% aqueous solution) was dropped under a reduced pressure (80° to 90° C./100 to 130 mmHg). After completion of the dropping, the reaction mixture was aged for 3 hours and filtered, followed by removal of the solvent, addition of a 10% NaOH aqueous solution to remove hydrolyzing chlorine and washing with water to obtain 256 g of compound D of the following formula with an epoxy equivalent of 188 (theoretical: 176) at a yield of 91%. The IR absorption spectra are shown in FIG. 3. The attributions of NMR spectra are shown below.

Compound D

NMR spectra (solvent: $(CD_3)_2CO$, ppm($\delta$)):

1.4: $-CH=CH-C\underline{H}_3$

-continued 2.65: $-C\underline{H}-C\underline{H}_2$ (epoxide)

3.2: $-C\underline{H}-C\underline{H}_2$ (epoxide)

4.2: $-C\underline{H}_2-CH-CH_2$ (epoxide)

6.7-8.3: $-[C_{10}\underline{H}_4]$, $-C\underline{H}=C\underline{H}-CH_3$

Experiment 35 parts by weight of compound D of the present invention and 35 parts by weight of N,N'-4,4'-diphenylmethane bismaleimide were provided along with ingredients indicated in Table 1. The resultant mixture was uniformly melted and mixed by means of hot two rolls to obtain thermally curable resin composition I. For comparison, compound E of the following formula was prepared, followed by repeating the above procedure except that compound E was used instead of compound D, thereby obtaining thermally curable resin composition II.

Compound E (m = 2 to 6)

These thermally curable resin compositions were subjected to the following tests (a) to (d). The results are also shown in the Table.

(a) Spiral flow value

A mold as prescribed in the EMMI standards was used and the value was determined at 175° C. at a pressure of 70 kg/cm².

(b) Mechanical strength (bending strength and flexural modulus)

A 10×4×100 mm bar was made by a method as prescribed in JIS-K6911 under conditions of 175° C., 70 kg/cm² and a molding time of 2 minutes, and post-cured at 180° C. for 4 hours, followed by measurement at 25° C.

(c) Glass transition temperature

A 4 mm φ×15 mm test piece was used and the transition temperature was measured by heating at a rate of 5° C./minute by means of a dilatometer.

(d) High temperature and high humidity environmental test

A 50 mm φ×3 mm test piece was allowed to stand under conditions of 121° C. and 2 atmospheric pressures for 24 hours, after which its water absorption was measured.

TABLE 1

| Thermally Curable Resin Composition | I | II |
|---|---|---|
| Composition (parts by weight): | | |
| N,N'-4,4'-diphenylmethane bismaleimide | 35.0 | 35.0 |
| Reaction product: | | |
| compound D | 35.0 | |

TABLE 1-continued

| Thermally Curable Resin Composition | I | II |
|---|---|---|
| compound E | | 35.0 |
| Phenolic resin (OCN7000) | 19.0 | 19.0 |
| Triphenylphosphine | 0.8 | 0.8 |
| Curing catalyst | 3.0 | 3.0 |
| Dicumyl peroxide | 0.45 | 0.45 |
| Quartz powder | 270.0 | 270.0 |
| γ-glycidoxypropyltrimethoxysilane | 0.8 | 0.8 |
| Wax E | 0.8 | 0.8 |
| Flame retardant | 8.6 | 8.6 |
| Aid for flame retardancy | 8.0 | 8.0 |
| Carbon black | 1.0 | 1.0 |
| Test results: | | |
| Spiral flow (cm) | 78.0 | 50.0 |
| Bending strength (kg/cm² at 25° C.) | 13.5 | 12.2 |
| Glass transition temperature (°C.) | 208 | 190 |
| Water absorption (%) | 0.70 | 0.90 |

Curing catalyst: melt mixture of DBU:TD2131=2:8
DBU: diazabicycloundecene
OCN7000: product of Nippon Kayaku Co., Ltd.
TD2131: phenol novolac resin (product of Dainippon Inks Co., Ltd.)

From the results of the above Table, the curable resin composition comprising the naphthalene derivatives of the present invention has the fluidity better than the naphthalene derivative-free composition, with a higher bending strength, a higher glass transition temperature and a lower water absorption.

Thus, the allyl or propenyl group-containing naphthalene derivatives of the present invention exhibit good working properties and are highly reactive with other epoxy resins, phenolic resins, maleimide resins and the like. In addition, the cured products obtained from compositions comprising the derivatives have good heat resistance and mechanical strength at high temperatures and are resistant to heat deterioration over a long term with a low water absorption and a high degree of hardness. Thus, the allyl or propenyl group-containing naphthalene derivatives of the invention are effectively utilizable as an ingredient of various resin compositions and also as an modifier for various resins.

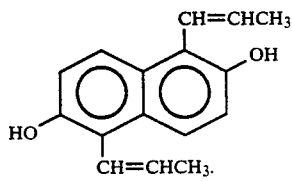

What is claimed is:

1. A compound of the formula